United States Patent [19]

Dalton

[11] Patent Number: 4,657,033
[45] Date of Patent: Apr. 14, 1987

[54] DENTAL FLOSS HOLDER
[76] Inventor: Paul V. Dalton, 7008 7th Avenue Blvd., NW., Bradenton, Fla. 33529
[21] Appl. No.: 869,373
[22] Filed: Jun. 2, 1986
[51] Int. Cl.⁴ .............................................. A61C 15/00
[52] U.S. Cl. ...................................................... 132/91
[58] Field of Search ................... 132/91, 92 R, 90, 89; 433/161

[56] References Cited
U.S. PATENT DOCUMENTS 3,472,247 10/1969 Borsun et al. .......................... 132/91
3,863,655 2/1975 Smith ..................................... 132/91

Primary Examiner—Robert Peshock
Attorney, Agent, or Firm—Charles J. Prescott

[57] ABSTRACT

A dental floss holder of integral, molded construction and including an elongated handle and a wishbone-shaped portion forwardly disposed at an acute angle of greater than forty five degrees to the axis of the handle. The handle is comprised of a gripping portion and a necked down portion from which the wishbone portion is disposed. The wishbone portion includes a pair of prongs shaped to form a generally wishbone configuration adapted to straddle the width and height of the user's teeth. Each prong has a groove disposed adjacent the distal end and transversely cut part way into the prongs. In the preferred embodiment, one groove faces forwardly while the other groove faces rearwardly, the groove being tapered to lockably receive at least one wrap of dental floss therein and around so that the span of floss tensioned there between is generally tranversely oriented and spaced from the handle axis. The prongs are sufficiently resilient to allow the user to squeeze them together slightly during locking installation of the dental floss such that, where released thereafter, additional dental floss tensioning is achieved.

8 Claims, 9 Drawing Figures

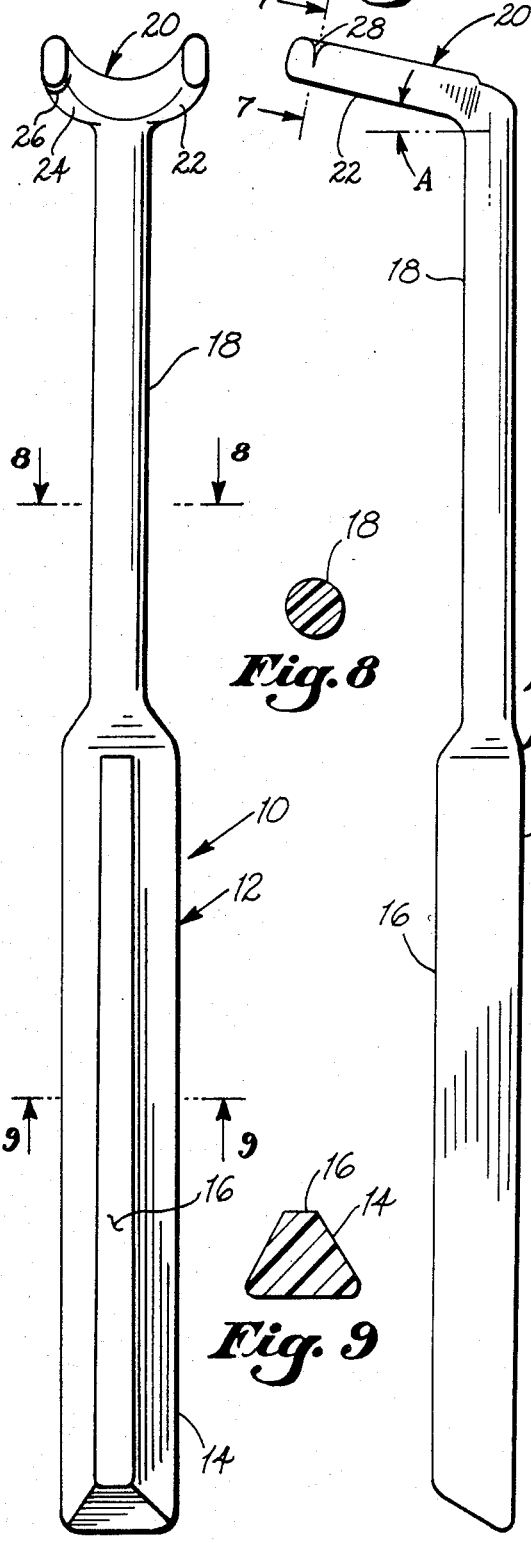
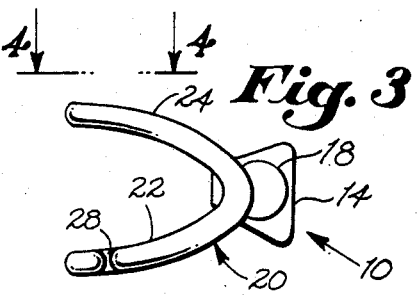
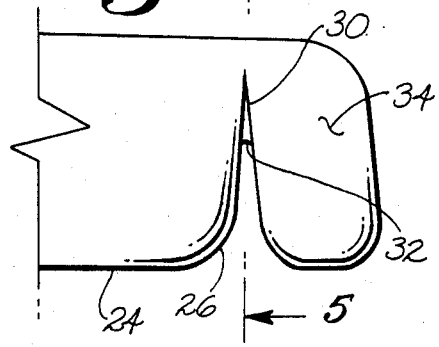
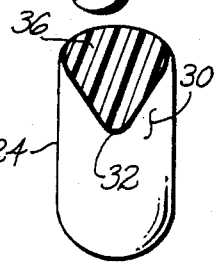
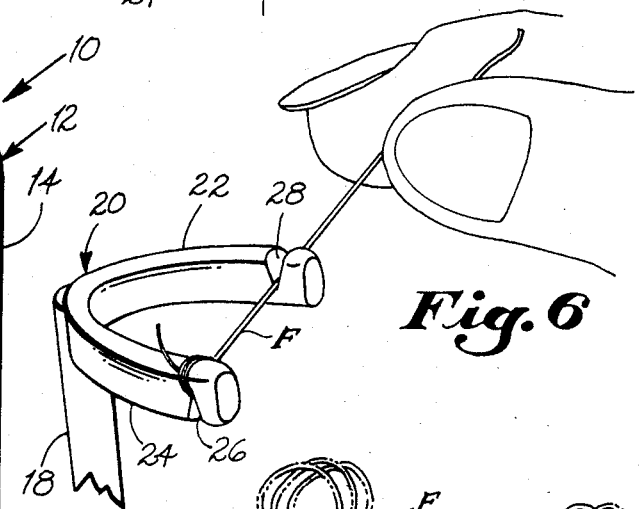
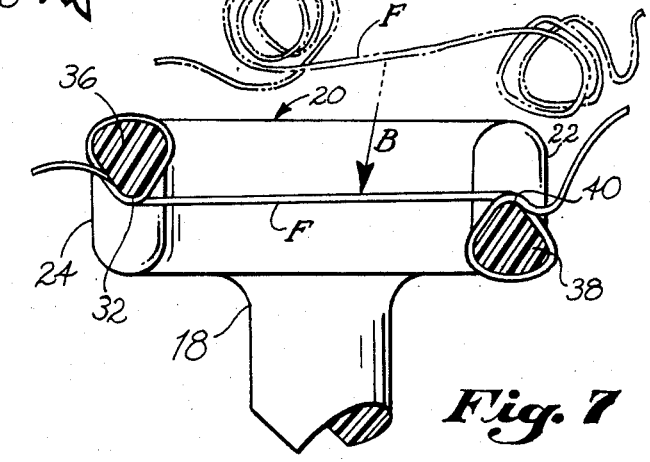

DENTAL FLOSS HOLDER

BACKGROUND OF THE INVENTION

This invention relates generally to oral hygiene devices and more particularly to dental floss holders adapted to retain a span of dental floss in tensioned fashion for the removal of plaque and food particles lodged between the teeth.

Plaque has become increasingly recognized as one of the major causes of dental and gum deterioration. Plaque is a soft, sticky, colorless film of bacteria constantly forming on the teeth and along the gum line. It is a combination of sugar and other carbohydrates which combines to form acids which attack tooth enamel and can even cause tooth cavities. Plaque can also lead to inflammation of the gums (gingivitis) which is identified by swollen, bleeding gums. Gingivitis can lead to periodontitis and receding of the gums and, ultimatly bone deterioration.

Minerals in saliva combine with plaque at the tooth surface and harden into a rough, insightly deposit called calculus or tarter. Calculus formations provide a coarse surface to which more plaque may adhere, accelerating plaque growth. Once calculus has formed, it generally is only removable through professional dental prophylaxis.

In addition to regular tooth brushing, flossing between and around the teeth and gums is a generally accepted and widely recommended procedure. Dental floss is a string-like waxed or unwaxed material which usually comes in rolls or spools. Flossing is especially effective in removing plaque and food debris in hard-to-reach areas and slightly under the gumline. Flossing involves breaking through the interproximal contact points where plaque and stringy food are trapped and also between adjacent teeth.

An early and well known mode of forcing the tensioned dental floss between and around teeth and gums is to wrap a length around the end of one finger of each hand. This procedure is cumbersome and wastes considerable amounts of dental floss material.

A number of devices are known to applicant which, in the past, have been provided to supposedly assist the user in dental flossing between teeth. One such early device is disclosed in U.S. Pat. No. 2,873,749 to Gjerde which provides a slidable rachet means along the handle for tensioning the floss spanned between opposing forked members. Another such floss holder is disclosed in U.S. Pat. No. 3,871,392 to Thomas. This device provides a groove at the base of the forked members for retaining the floss once tensioned. Two designs for such floss holders are disclosed in U.S. Pat. Nos. Des. 240,831 and 244,541. A multi-spanned dental flossing device is disclosed in U.S. Pat. No. 4,440,184.

For various reasons of impracticality, less than adequately adapted structure for convenient and effective use, or inadequate floss tensioning means or retention, none of the prior art above cited has met with commercial acceptance. One particular shortcoming of many of these devices is that, in the process of dental flossing, the user must exert vigorous lateral forces on the span of floss in virtually all directions in relation to the supporting and retaining structure for the length of floss. This, many times leads either disengagement or loosening of the dental floss.

The present invention provides a simple, yet highly effective integrally molded dental floss holder which includes structure which will retain a very short length of dental floss material in a locked relationship spanning between opposing fork members which may be then manipulated in any direction during the flossing operation. The forked members have a unique wishbone-shape which is intended is provide just sufficient clearance to span and straddle the user's teeth but will minimize the size and mass of the structure which is inserted into the user's mouth. This wishbone structure is also adapted to be resiliently hand-compressed during floss installation to increase tensioning of the floss for use when released.

BRIEF DESCRIPTION OF THE INVENTION

This invention is directed to a dental floss holder of integral, molded construction and including an elongated handle and a wishbone-shaped portion forwardly disposed at an acute angle of greater than forty five degrees to the axis of the handle. The handle is comprised of a gripping portion and a necked down portion from which the wishbone portion is disposed. The wishbone portion includes a pair of prongs shaped to form a generally wishbone configuration adapted to straddle the width and height of the user's teeth. Each prong has a groove disposed adjacent the distal end and transversely cut part way into the prongs. One groove, in the preferred embodiment, faces forwardly while the other groove faces rearwardly, the groove being tapered to lockably receive at least one wrap of dental floss therein and around so that the span of floss tensioned therebetween is generally tranversely oriented and spaced from the handle axis. The prongs are sufficiently resilient to allow the user to squeeze them together slightly during locking installation of the dental floss such that, where released thereafter, additional dental floss tensioning is achieved.

It is therefore an object of this invention to provide an inexpensive integrally molded lightweight dental floss holder which may be conveniently used in conjunction with short lengths of dental floss to floss the user's teeth.

It is another object of this invention to provide a unique wishbone-shaped design in conjunction with a laterally disposed pair of opposing prongs which are adapted to conveniently fit over and around the user's teeth during flossing while minimizing the size of that portion of the dental floss holder which is inserted into the user's mouth.

It is another object of this invention to provide uniquely positioned and shaped grooves adjacent the distal ends of the prongs which are opposingly facing forwardly and rearwardly to provide lockable interengagement of the dental floss therearound and therebetween and so that the span of dental floss may be laterally exerted in any direction without any disengagement from the grooves.

It is another object of this invention to provide unique wishbone-shaped prongs which may be resiliently flexed inwardly by finger squeezing during dental floss installation to result in increased floss tensioning when the prongs are released.

In accordance with these and other objects which will become apparent hereinafter, the present invention will now be described with reference to the accompanying drawings in which:

BRIEF DESCRIPTION OF THE DRAWINGS

FIG. 1 is a top plan view of the invention.

FIG. 2 is a right side elevation view of the invention.

FIG. 3 is a front end elevation view of the invention.

FIG. 4 is a view in the direction of arrows 4—4 in FIG. 3.

FIG. 5 is a section view in the direction of arrows 5—5 in FIG. 4.

FIG. 6 is a perspective view of the wishbone portion of the invention depicting installation of a length of dental floss.

FIG. 7 is a section view in the direction of arrows 7—7 in FIG. 2 and symbolically depicting installation of a length of dental floss.

FIG. 8 is a section view in the direction of arrows 8—8 in FIG. 1

FIG. 9 is a section view in the direction of arrows 9—9 in FIG. 1.

DETAILED DESCRIPTION OF THE INVENTION

Referring now to the drawings, and particularly to FIGS. 1-3 and 8 and 9, the dental floss holder is shown generally at numeral 10 and includes a handle 12 and a wishbone portion 20 disposed at one end of the handle 12. The handle 12 comprises a gripping portion 14 and a necked down portion 18. The enlarged gripping portion 14, having a generally triangular cross section as shown in FIG. 9, also has a flat upper edge 16 for improved gripping and manipulation control. The necked down portion 18 has a circular cross section as seen in FIG. 8 of reduced size in relation to the gripping portion 14 to enhance the holder's ability to be manipulated in the user's mouth.

The wishbone portion 20 is integral with the end of the necked down portion 18 and includes a pair of opposing prongs 22 and 24 which are cooperatively disposed to form a generally wishbone shape. As may be best seen in FIG. 3, this unique wishbone shape is adapted to straddle over the top of the user's teeth. The prongs 22 and 24 lie in a plane which is perpendicular to the axis of the handle 12 as viewed in FIG. 1, and disposed slightly forwardly at an angle A from perpendicular to the handle 12 axis as viewed in FIG. 2. This forwardly angle A is less than forty five degrees, and preferably in the range of ten to fifteen degrees in order to further enhance the holder's ability to be manipulated within the user's mouth during flossing. Note that all edge and end contours, particularly of the wishbone portion 20, are rounded so as to prevent or reduce the possibility of injury to the user's gums.

Referring now also to FIGS. 4 and 5, a pair of grooves 26 and 28 are provided cut part way into the prongs 24 and 22 respectively slightly adjacent the distal ends of the prongs 24 and 22. These grooves 26 and 28 are disposed generally perpendicularly to the length of the prongs 24 and 22 and are uniquely disposed perferrably in oppositely facing forwardly and rearwardly directions as shown. Groove 26 is rearwardly facing, while groove 28 is forwardly facing, the purpose of which will be described herebelow. Grooves 26 and 28 are generally inwardly tapering to apex 32 of groove section 36, apex 38 of groove section 38 in FIG. 7, and also extend further into the distal end 34 of each prong 22 and 24 at 30. Because of the inwardly tapering side contour of these grooves 26 and 28, the extended groove portion 30 forms a sharp wedge as best seen in FIG. 4.

Turning now to FIGS. 6 and 7, the preferred mode of usage of the present invention is depicted. A short length of dental floss F, having been cut from a supply or roll thereof, is first held at one end by the user who then wraps the dental floss F around one prong 24 in groove 26 as shown. Although one wrap or turn of dental floss appears to be sufficient to lock this wrap of dental floss in place, two or three wraps of the floss within the first groove 26 or 28 chosen is preferred. After the first wrap or series of wraps is locked in place around the first chosen prong e.g. 24, the length of floss is then tensioned between the grooves 26 and 28 as shown in FIG. 6. Thereafter, one or a series of wraps is made by the floss within that next groove 28 and, thusly, locked therein also.

Referring again particularly to FIGS. 4, 5, 6, and 7, it should be now clearly understood that the tapering grooves 26 and 28, having extended portions 30 which terminate in a sharp wedge configuration serve to releasably lock one or more wraps of dental floss wrapped and tensioned there around.

An additional and important feature of the present invention is in the preferrably oppositely disposed orientation of grooves 26 and 28. As best shown in FIGS. 6 and 7, groove 26 is rearwardly disposed, while groove 28 is forwardly disposed. This orientation provides for either the right-handed or left-handed user the benefit of wrapping the floss around both prongs in the same initial continuous rotational motion of the free hand while also providing a span of dental floss between the grooves which is virtually precisely transverse to the axis of the handle for more accurate manipulation of the handle and tensioned dental floss F. This transverse positioning of the dental floss F between the grooves 26 and 28 is achieved by the similar transverse orientation of the apxes 32 and 40 as best seen in FIG. 7.

A further important aspect of the present invention resides in the flexibility or resiliency of the prongs one to another. In the process of wrapping the floss F around each prong 22 and 24 and within each groove 28 and 26, the user may compressively squeeze the prongs 22 and 24 together slightly by finger pressure. After the floss F has been lockably secured within each groove 26 and 28, release of this inward biasing of the prongs 22 and 24 will create additional tension on the span of floss there between, thus further improving the usability of this invention and ease with which lengths of floss may be repeatedly installed for more effective use of the dental floss F.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A dental floss holder comprising:
   an elongated handle and an integral wishbone-shaped portion disposed at one end of said handle;
   said handle having a gripping portion and a necked down portion;
   said wishbone portion having a pair of opposing symetrically and divergently extending prongs forwardly disposed from the end of said necked down portion at an acute angle of greater than ninety degrees to the axis of said handle;

said pair of prongs shaped to form a generally wishbone configuration adapted to straddle the width and height of the user's teeth;

each said prong having a groove adjacent the distal end of, and transverse to, each said prong;

said grooves shaped to lockably receive at least one wrap of dental floss around said prong and into said groove;

the bottom of said grooves and said grooves are disposed in tranverse relationship one to another and spaced from said handle axis such that the segment of lockably wrapped dental floss there between is disposed generally transversely between said prongs.

2. A dental floss holder as set forth in claim 1, wherein:
one said groove is forwadly facing and the other said groove rearwardly facing.

3. A dental floss holder as set forth in claim 2, wherein:
said acute angle is about eighty degrees.

4. A dental floss holder as set forth in claim 2, wherein:
said dental floss holder is integrally molded of plastic.

5. A dental floss holder as set forth in claim 2, wherein:
said grooves are tapered toward said bottom for increased wedging and locking of dental floss wrapped therein.

6. A dental floss holder as set forth in claim 2, wherein:
said necked down portion is cylindrical and circular in cross section;
said gripping portion is cylindrical and generally triangular in cross section and having a flat along the upwardly edge for increased gripping and manipulation of said dental floss holder.

7. A dental floss holder as set forth in claim 6, wherein:
all edge and corner contours of said prongs are rounded to reduce mouth and gum tissue injury during use.

8. A dental floss holder as set forth in claim 1, wherein:
said wishbone-shaped portion is sufficiently resilient to allow the user to squeeze said prongs toward one another during installation of the dental floss around said prongs and into said grooves for increased tension of the dental floss when the user's squeezing pressure is released.

* * * * *